United States Patent [19]

Rath et al.

[11] 4,235,412
[45] Nov. 25, 1980

[54] TUBE CLAMPING DEVICE

[75] Inventors: Lucien M. Rath, Milwaukee; W. Martin Schultze, New Berlin, both of Wis.

[73] Assignee: Plastronics, Inc., Milwaukee, Wis.

[21] Appl. No.: 955,810

[22] Filed: Oct. 30, 1978

[51] Int. Cl.³ .............................................. F16K 7/06
[52] U.S. Cl. ................................... 251/10; 24/132 R
[58] Field of Search ............................ 251/9, 10, 4; 24/255 SL, 132 R

[56] References Cited

U.S. PATENT DOCUMENTS

| | | | |
|---|---|---|---|
| 350,850 | 10/1886 | Tatum | 251/10 |
| 3,822,052 | 7/1974 | Lange | 251/10 |
| 3,874,042 | 4/1975 | Eddleman et al. | 251/10 X |
| 4,053,135 | 10/1977 | Saliaris | 251/10 |

Primary Examiner—Martin P. Schwadron
Assistant Examiner—Richard Gerard
Attorney, Agent, or Firm—Michael, Best & Friedrich

[57] ABSTRACT

A clamping device for a fluid conduction tube comprises first, second, and third body members which are pivotally interconnected for movement between a generally flat, unfolded position and a folded together position in which the first and second body members generally face each other, and the third body member is generally perpendicularly disposed therebetween. The device may be slidably attached to the tube when the body members are in the unfolded position, and, when the device is in the folded together position, a portion of the tube is clamped between the first and second body members, thereby effectively blocking fluid conduction through the tube.

1 Claim, 5 Drawing Figures

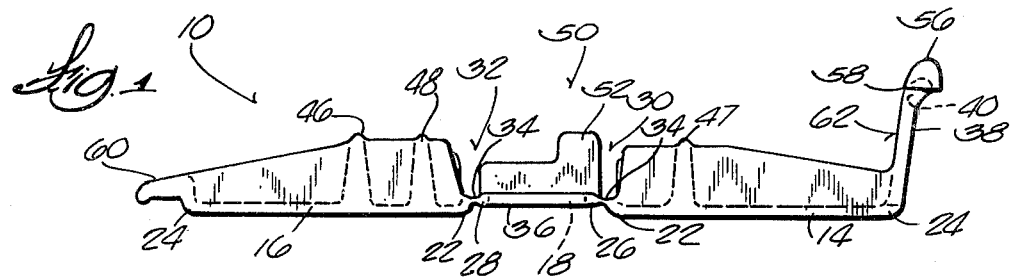
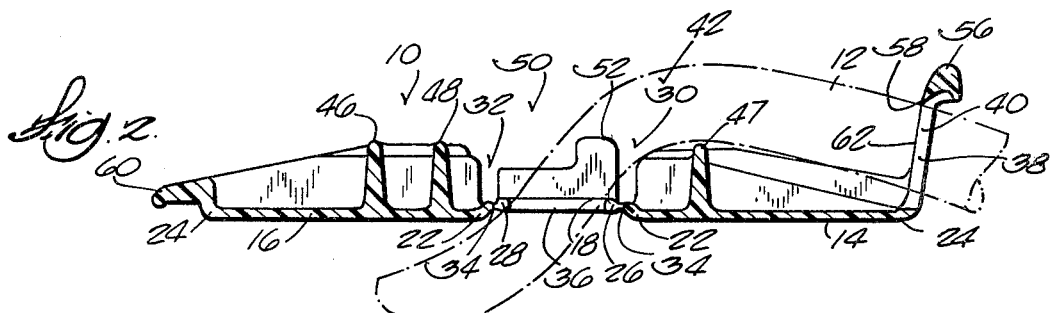
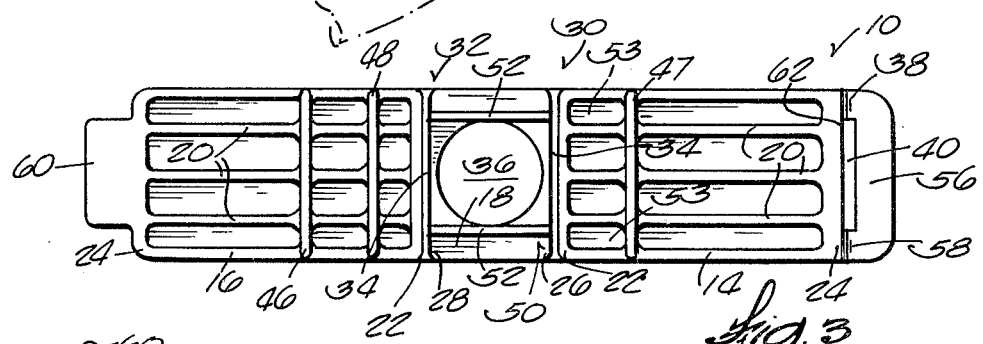
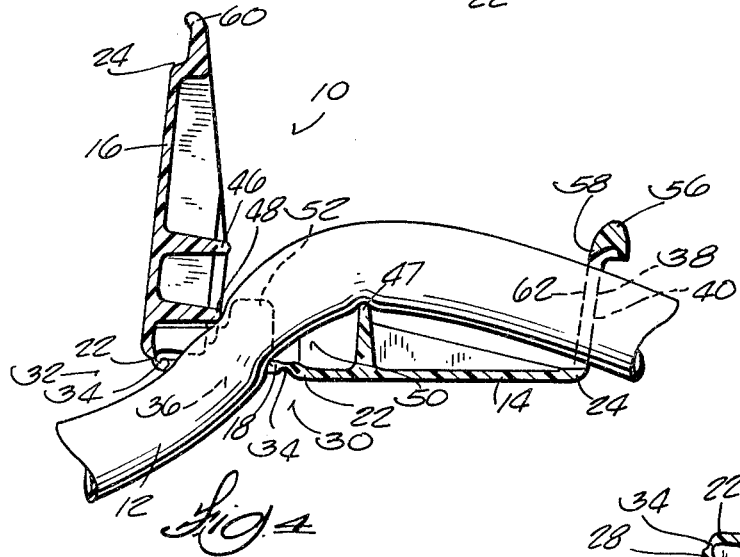
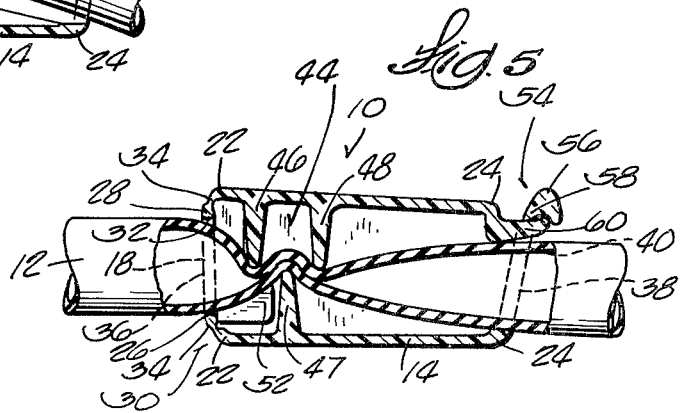

TUBE CLAMPING DEVICE

BACKGROUND OF THE INVENTION

I. Field of the Invention

This invention relates generally to tube clamping devices.

II. Description of the Prior Art

Small, lightweight tube clamping devices are well known, a representative example of which is disclosed in U.S. Pat. No. 3,512,227 issued to Alois A. Krawagna on May 19, 1970.

It is desirable to be able to prevent free sliding movement of a tube clamping device along the tube when the device is in its open or unclamped position, which thereby permits selective positioning of the device along the tube. This prevents loss or misplacement of the device, as well as permits quick operation of the device should it be necessary to clamp the tube.

In prior constructions, the structure which prevents free sliding movement of the device along the tube when the device is in the unclamped position does so be creating constrictions in the tube which interfere with the desired free flow of fluid. Furthermore, prior constructions do not assure that the tube is properly aligned with the crimping mechanism so as to prevent fluid leaks in the tube caused by incomplete clamping.

SUMMARY OF THE INVENTION

It is one of the objects of this invention to permit the slidable attachment of a clamping device along a tube when the device is in the unclamped position without thereby constricting the free flow of fluid.

It is another object of the invention to assure that the tube is properly aligned in the clamping device when it is necessary to clamp the tube shut, thereby preventing unwanted fluid leaks therethrough.

To achieve these and other objects, the invention provides a clamping device for a fluid conduction tube comprising first, second, and third body members, and hinge means for pivotally interconnecting the body members for movement between an unfolded position in which the body members are disposed in a generally coplanar relationship and a folded together position in which the first and second body members are disposed in a generally facing relationship and the third body member is generally perpendicularly disposed therebetween. Fastening means is provided for slidably attaching the device upon the tube when the body members are in the unfolded position. Crimp means is provided such that, when the body members are in the folded together position, a portion of the tube is clamped to a restricted position between the first and second body members, thereby effectively blocking fluid conduction through the tube.

In one embodiment of the invention, the device includes guide means for aligning the tube with the crimp means when all of the body members are moved from the unfolded position to the folded together position. In this embodiment, latching means are provided for selectively locking all of the body members in the folded together position.

In the preferred embodiment, the first and second body members both include inner and outer edges, and the third body member includes first and second side edges. The hinge means includes a first resilient plastic webbing which pivotally connects the inner edge of the first body member with the first side edge of the third body member, and a second resilient plastic webbing which pivotally connects the inner edge of the second body member with the second side edge of the third body member. In this embodiment, the third body member includes a first hole of a fixed size which freely accommodates the tube, and the first body member includes an upstanding shoulder extending from the outer edge and having a second hole of a fixed size which also freely accommodates the tube. When the tube is weaved through the first and second holes, free sliding movement of the device along the tube is prevented when the body members are in the unfolded position.

Also in the preferred embodiment, the crimp means includes a spaced pair of parallel ridges located on the second body member and a single ridge located on the first body member for registry with the spaced pair of ridges when all of the body members are in the folded together position. The guide means includes a pair of upstanding ribs located tangentially along the first hole in the third body member, which prevents linear displacement of the tube in the device when the device is in the unfolded position, thereby assuring proper alignment of the tube between the crimping ridges.

Also in the preferred embodiment, the latching means includes a tab extending laterally outwardly of the outer edge of the second body member, and a lip formed on the upstanding shoulder and adapted for snap-fit engagement with the tab when all of the body members are moved from the unfolded position to the folded together position. In this embodiment, the device and all parts thereof are plastic.

DESCRIPTION OF THE DRAWINGS

FIG. 1 is a side view of a tube clamping device in which the device is shown in the flat, or unfolded position;

FIG. 2 is a sectional side view of the tube clamping device of FIG. 1, showing the passage of a fluid conduction tube through the device;

FIG. 3 is a top view of the tube clamping device of FIG. 1;

FIG. 4 is a sectional side view of the tube clamping device of FIG. 2, in which the device is shown in a partially folded together position; and FIG. 5 is a sectional side view of the tube clamping device of FIG. 2, in which the device is shown locked in its fully folded together position with the tube clamped.

DESCRIPTION OF THE PREFERRED EMBODIMENT

A tube clamping device 10 is shown in FIG. 1. While the device 10 is applicable for use in a diverse variety of environments, the device 10 finds wide application to shut-off the bottom drain tube of a urinary collection bag. The tube is made of latex, and is used to drain the bag after recording the quantity of urine collected.

Referring specifically to the structure of the device 10 shown in FIG. 1, distinct first, second, and third body members 14, 16, and 18 are all pivotally interconnected. While the body members 14, 16, and 18 may be variously constructed, they are preferably formed of injection molded polyprophylene plastic. As is shown in FIG. 3, integral stiffener ribs 20 are formed on the first and second body members 14 and 16 for additional strength.

The first and second body members 14 and 16 include inner and outer edges 22 and 24, and the third body member 18 includes oppositely spaced first and second side edges 26 and 28. The inner edge 22 of the first body member 14 is connected by a hinge 30 with the first side edge 26 of the third member 18, and the inner edge 22 of the second body member 16 is similarly connected by another hinge 32 with the second side edge 28 of the third member 18. While the hinges 30 and 32 may be variously formed, in the illustrated embodiment, a flexible plastic web or joint 34 connects the first and second body members 14 and 16 with the third body member 18.

By virtue of this double-jointed construction, the first and second body members 14 and 16 are both independently pivotal relative to the intermediate third body member 18. The body members 14, 16, and 18 are thereby movable between a flat or unfolded position, as shown in FIGS. 1 through 3, and a folded together position, as shown in FIG. 5. As can be seen in FIG. 5, when the folded together position, the first and second body members 14 and 16 generally face each other, and the third body member 18 is perpendicularly disposed therebetween.

When being used as part of a urinary collection system, it is desirable to movably attach the device 10 upon the tube 12 so that the device 10 is readily accessible for use and is not subject to misplacement or loss. For this purpose, the third body member 18 includes a hole 36 of fixed size centrally located between the first and second side edges 26 and 28. The hole 36 freely accommodates passage of the tube 12 so as not to create constrictions in the tube 12 which would interfere with the passage of fluid therethrough. The first body member 14 includes an upstanding shoulder 38 extending from the outer edge 24 and having another hole 40 of fixed size also adapted to freely accommodate passage of the tube 12.

As shown in FIG. 2, the tube 12 is easily weaved through both holes 36 and 40 when the body members 14, 16, and 18 are in the unfolded position. Furthermore, due to the relative placement of the holes 36 and 40, a slight bend 42 is formed in the tube 12 intermediate the two holes 36 and 40. The bend 42 prevents free sliding movement of the unfolded device 10 along the tube 12 without at the same time creating constrictions in the tube 12 which would interfere with the passage of fluid therethrough. Should location of the device 10 along the tube 12 be desired, an operator may easily slide the device 10 along the tube 12 to the desired location.

When it is necessary to crimp the tube 12 to prevent passage of fluid therethrough, the unfolded device 10 is placed into its folded together position. As shown in FIG. 5, a portion of the tube 12 is thereby confined between the first and second body members 14 and 16 intermediate the two holes 36 and 40. The device 10 includes crimp means 44 for clamping the confined portion of the tube 12 to block the passage of fluid therethrough.

While the crimp means 44 may be variously constructed, in the illustrated embodiment (as best shown in FIG. 5), a spaced pair of parallel ridges 46 and 48 are located on the second body member 16, and a single ridge 47 is similarly formed on the first body member 14. When the body members 14, 16, and 18 are moved to their folded together position, the single ridge 47 registers with the pair of ridges 46 and 48, thereby forming a crimp in the tube 12 between the pair of ridges 46 and 48.

In order that the crimped portion of the tube 12 effectively blocks the passage of fluid through the tube 12, it is necessary that the entire tube 12 be properly aligned with the crimping ridge members 46, 47, and 48. Misalignment could result in an incomplete crimp and fluid leakage through the tube 12.

In accordance with the invention, guide means 50 is provided to urge the tube 12 into correct alignment with the crimping ridge members 46, 47, and 48 when the body members 14, 16, and 18 are moved between the unfolded and folded together position. While the guide means 50 may be variously constructed, in the illustrated embodiment, a pair of upstanding guide ribs 52 are located tangentially along the hole 36 in the third body member 18. The guide ribs 52 prevent lateral displacement of the tube 12 between the two holes 36 and 40 as the body members 14, 16, and 18 are being moved between the unfolded and folded together positions, thereby assuring that the tube 12 is properly aligned with the crimping ridge members 46, 47, and 48 when the body members 14, 16, and 18 reach the folded together position. As best shown in FIG. 3, the guide ribs 52 fit in registry with channels 53 formed between the stiffening ribs 20 on the first body member 14 when the body members 14, 16, and 18 are placed in the folded together position.

Latching means 54 is provided for locking the device 10 in the folded together position. More particularly, the upstanding shoulder 38 is made of a resilient material, such as the polyprophylene plastic of which the body members 14, 16, and 18 are molded, and a lip 56 is formed on the uppermost end 58 of the shoulder 38. The second body member 16 includes a tab 60 extending laterally outwardly of the outer edge 24. As the body members 14, 16, and 18 are moved from the unfolded position to the folded together position, the tab 60 bears against the inner portion 62 of the resilient shoulder 38 and ultimately makes snap-fit engagement with the underbody of the lip 56 when the folded together position is reached. Manual displacement of the resilient shoulder 38 frees the tab 60 of its snap-fit engagement with the lip 56 and permits return of the body members 14, 16, and 18 to the unfolded position.

I claim:

1. A clamping device for a fluid conduction tube comprising:

a first body member having an inner edge and an outer edge, an upstanding shoulder of resilient material extending from said outer edge and having a hole of fixed size adapted to freely accommodate the tube, said upstanding shoulder including a downwardly facing retaining lip formed thereon, said lip defining the upper edge of said hole;

a second body member having an inner edge and an outer edge, a tab extending laterally outwardly of said outer edge of said second body member, said tab adapted for snap engagement with said retaining lip on said upstanding shoulder when said clamping device is in its folded together closed position;

a third body member having first and second side edges and a hole of fixed size adapted to freely accommodate the tube centrally located between said side edges, said third body member further including a pair of upstanding guide ribs located tangentially along said hole in said third body member;

a first resilient hinge pivotally connecting said inner edge of said first body member with said first side edge of said third body member;

a second resilient hinge pivotally connecting said inner edge of said second body member with said second side edge of said third body member;

said first, second and third body members being pivotally movable along said first and second resilient hinges between an unfolded position in which said first, second and third body members are disposed in a generally coplanar relationship and the tube passes through said holes in said first and third body members, thereby movably attaching said device upon the tube, and a folded together position in which said first and second body members generally face each other with said tab and said lip in snap-fit engagement, said third body member being generally perpendicularly deposed therebetween and a portion of the tube being confined between said first and second body members intermediate said holes in said first and third body members; and crimp means for clamping said confined portion of the tube, thereby effectively blocking fluid conduction through the tube, said crimp means including a spaced pair of parallel ridges located on said second body member and a single ridge located on said first body member and registering with said pair of ridges when said first, second, and third body members are in said folded together position.

* * * * *

UNITED STATES PATENT AND TRADEMARK OFFICE
CERTIFICATE OF CORRECTION

PATENT NO. : 4,235,412
DATED : November 25, 1980
INVENTOR(S) : Lucien M. Rath and Martin Schultze It is certified that error appears in the above-identified patent and that said Letters Patent are hereby corrected as shown below:

Column 1, Line 22,     After "does so" delete "be" and substitute therefor ---by---

Column 3, Line 21,     After "when" and before "the" insert ---in---

Column 4, Line 64, Claim 1,    After "tube" and before "located" delete "centerally" and substitute therefor ---centrally---

Column 6, Line 2, Claim 1,    After "perpendicularly" delete "deposed" and substitute therefor ---disposed---

Signed and Sealed this

Tenth Day of March 1981

[SEAL]

Attest:

RENE D. TEGTMEYER

Attesting Officer     Acting Commissioner of Patents and Trademarks